(12) United States Patent
Yamashita et al.

(10) Patent No.: US 8,542,957 B2
(45) Date of Patent: Sep. 24, 2013

(54) OPTICAL WAVEGUIDE SENSOR AND MANUFACTURING METHOD OF THE SAME

(75) Inventors: Shuichi Yamashita, Okazaki (JP); Yukihiro Takeuchi, Miyoshi (JP)

(73) Assignee: Denso Corporation, Kariya (JP)

( * ) Notice: Subject to any disclaimer, the term of this patent is extended or adjusted under 35 U.S.C. 154(b) by 281 days.

(21) Appl. No.: 13/086,455

(22) Filed: Apr. 14, 2011

(65) Prior Publication Data

US 2011/0268385 A1 Nov. 3, 2011

(30) Foreign Application Priority Data

Apr. 28, 2010 (JP) ................................ 2010-103181

(51) Int. Cl.
*G02B 6/10* (2006.01)
(52) U.S. Cl.
USPC .......................................................... 385/12
(58) Field of Classification Search
USPC .................................................... 385/12–13
See application file for complete search history.

(56) References Cited

U.S. PATENT DOCUMENTS

| | | |
|---|---|---|
| 2004/0240768 A1 | 12/2004 | Depeursinge et al. |
| 2006/0013547 A1* | 1/2006 | Kitano et al. ................. 385/124 |
| 2006/0060788 A1 | 3/2006 | Uchida et al. |
| 2009/0103852 A1 | 4/2009 | Hamamoto |

FOREIGN PATENT DOCUMENTS

| | | |
|---|---|---|
| EP | 1 918 693 | 5/2008 |
| JP | A-2005-061904 | * 3/2005 |
| JP | A-2005-61904 | 3/2005 |
| JP | A-2005-234319 | 9/2005 |
| JP | A-2006-43120 | 2/2006 |
| JP | A-2006-329680 | 12/2006 |
| JP | A-2008-116955 | 5/2008 |
| JP | A-2009-210312 | 9/2009 |

OTHER PUBLICATIONS

Office Action mailed Apr. 17, 2012 in corresponding JP Application No. 2010-103181 (and English translation).
A. Densmore et al. "Spiral-path high-sensitivity silicon photonic wire molecular sensor with temperature-independent response." *Optic Letters* vol. 33.6 (Mar. 15, 2008).

* cited by examiner

*Primary Examiner* — Jerry Rahll
(74) *Attorney, Agent, or Firm* — Posz Law Group, PLC

(57) ABSTRACT

An optical waveguide sensor includes a substrate and an optical waveguide. The optical waveguide includes a core and a lateral clad. The core extends in a spiral shape above a surface of the substrate. The lateral clad is disposed in a same layer as the core above the surface of the substrate and is in contact with either side surfaces of the core. At least a part of a surface of the core located opposite from the substrate is a transmission surface from which light leaks and is absorbed by a detected object.

8 Claims, 10 Drawing Sheets

OPTICAL WAVEGUIDE SENSOR AND MANUFACTURING METHOD OF THE SAME

CROSS REFERENCE TO RELATED APPLICATIONS

The present application is based on and claims priority to Japanese Patent Application No. 2010-103181 filed on Apr. 28, 2010, the contents of which are incorporated in their entirety herein by reference.

BACKGROUND OF THE INVENTION

1. Field of the Invention

The present invention relates to an optical waveguide sensor using an evanescent wave that leaks from a core of an optical waveguide. The present invention also relates to a manufacturing method of an optical waveguide sensor.

2. Description of the Related Art

JP-A-2005-61904 discloses an optical waveguide sensor using an evanescent wave that leaks from a core of an optical waveguide.

The optical waveguide sensor is made of a silicon-on-insulator (SOI) substrate. The optical waveguide includes a silicon thin-line core and a clad layer. The silicon thin-line core is formed by processing a silicon layer located on a buried oxide layer in the SOI substrate. The clad layer is made of silicon oxide and fills either ends of the silicon thin-line core.

An upper surface of the silicon thin-line core is exposed to an outside in a detection region. In the detection region, the silicon thin-line core is shuttles at predetermined intervals, that is, the silicon thin-line core is arranged in a meandering shape.

In the above-described optical waveguide sensor, a length of the silicon thin-line core can be secured while restricting a dimension by arranging the silicon thin-line core in the meandering shape, and thereby a detection sensitivity of the optical waveguide sensor is improved. In a case where the silicon thin-line core is arranged in the meandering shape, it is required to reduce a bending radius at a bent portion where a waveguide direction is changed in order to make a small and long waveguide.

When the bending radius is small, at the bent portion, an incident angle may be smaller than a critical angle and light may be easily transmitted from the core. Thus, in the above-described waveguide sensor, a difference in refractive index between the core made of single crystal silicon and the clad made of silicon oxide is increased so that a reflection angle is reduced and light is not easily transmitted from the core even at the bent portion.

However, when the reflection angle is reduced by increasing the difference in refractive index between the core and the clad, a loss generated at an interface due to scattering may be increased. Thus, the above-described optical waveguide sensor may have a large transmission loss and may have difficulty providing a small and long optical waveguide.

If the difference in refractive index between the core and the clad is reduced in the above-described configuration so as to increase the bending radius at the bent portion, the transmission loss can be reduced. However, because the silicon thin-line core is arranged in the meandering shape, increase in the dimension of the silicon thin-line core at each bent portion greatly influence the dimension of the optical waveguide sensor, and the dimension of the optical waveguide sensor is increased.

SUMMARY OF THE INVENTION

In view of the foregoing problems, it is an object of the present invention to provide an optical waveguide sensor that can have a high detection sensitivity and can have a small dimension. Another object of the present invention is to provide a method of manufacturing an optical waveguide sensor.

An optical waveguide sensor according to an aspect of the present invention includes a substrate and an optical waveguide. The optical waveguide includes a core and a lateral clad. The core extends in a spiral shape above a surface of the substrate. The lateral clad is disposed in a same layer as the core above the surface of the substrate and is in contact with either side surfaces of the core. At least a part of a surface of the core located opposite from the substrate is a transmission surface from which light leaks and is absorbed by a detected object.

Because the optical waveguide sensor uses the surface of the core located opposite from the substrate is used as the transmission surface, the optical waveguide sensor can restrict transmission loss and can have a high detection sensitivity compared with a case where the side surfaces of the core are used as the transmission surfaces. Furthermore, because the core extends in the spiral shape, a dimension of the optical waveguide can be reduced even when a bending radius at a bent portion is increased. Therefore, the optical waveguide can have a small dimension.

A manufacturing method according to another aspect of the present invention includes forming a core above a substrate, and forming a lateral clad being in contact with either side surfaces of the core in a same layer as the core above the substrate by depositing. When the lateral clad is formed, a composition of material for forming the lateral clad is changed continuously or in a stepwise manner so that a refractive index of the lateral clad changes continuously or in a stepwise manner with a distance from the core in a predetermined region from a boundary with the core.

An optical waveguide sensor manufactured by the above-described method can restrict scattering of light at an interface between the core and the lateral clad because the refractive index of the lateral clad is changed continuously or in the stepwise manner from the distance from the boundary with the core. Thus, the above-described method can manufacture an optical waveguide sensor that has a high detection sensitivity.

BRIEF DESCRIPTION OF THE DRAWINGS

Additional objects and advantages of the present invention will be more readily apparent from the following detailed description of preferred embodiments when taken together with the accompanying drawings. In the drawings:

FIG. 3A to FIG. 3C are cross-sectional views showing a manufacturing method of the optical waveguide sensor according to the first embodiment;

FIG. 19A to FIG. 19E are cross-sectional views showing a manufacturing method of the optical waveguide sensor according to the fourth embodiment.

DETAILED DESCRIPTION OF THE PREFERRED EMBODIMENTS

First Embodiment

Figure 1:
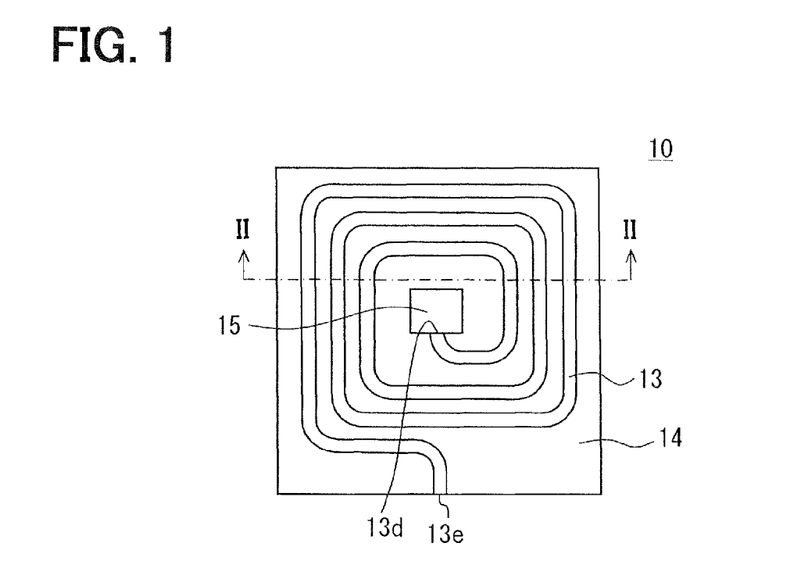
FIG. 1 is a plan view showing an optical waveguide sensor according to a first embodiment.
Figure 2:
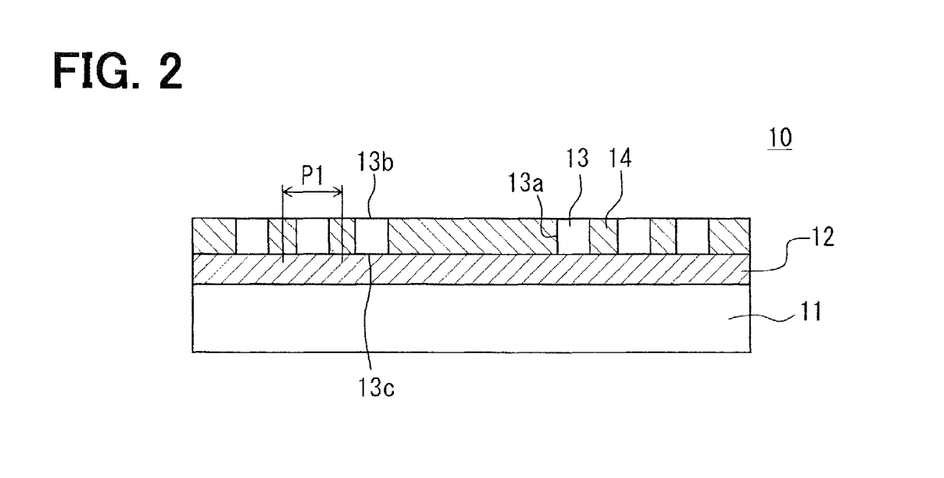
FIG. 2 is a cross-sectional view showing the optical waveguide sensor taken along line II-II in FIG. 1.

An optical waveguide sensor 10 according to a first embodiment of the present invention will be described with reference to FIG. 1 and FIG. 2.

The optical waveguide sensor 10 includes a substrate 11 and an optical waveguide formed above the substrate 11. The optical waveguide includes a core 13 and a lateral clad 14. The core 13 extends in a spiral shape above a surface of the substrate 11. The core 13 and the lateral clad 14 are located in the same layer above the surface of the substrate 11. The lateral clad 14 is in contact with either side surfaces 13a of the core 13, and the core 13 is disposed between the lateral clad 14. The core 13 has an upper surface 13b on an opposite side from the substrate 11. A part of the upper surface 13b provides a transmission surface from which an evanescent wave (evanescent light) leaks and is absorbed by a detected object. In the following description, a thickness direction of the substrate 11, that is, a direction perpendicular to the surface of the substrate 11 above which the core 13 and the lateral clad 14 are arranged is called simply "thickness direction."

The substrate 11 is made of single crystal silicon. On the surface of the substrate 11, a lower clad layer 12 is disposed so as to cover the whole area of the surface. On a surface of the lower clad layer 12 located on the opposite side from the substrate 11, the core 13 and the lateral clad 14 are disposed.

The core 13 is made of a material that has a higher refractive index than the lower clad layer 12 and the lateral clad 14. For example, the core 13 is made of silicon nitride. As shown in FIG. 1, the core 13 is arranged in the spiral shape. In other words, the core 13 has an inner end 13d located at the innermost position and an outer end 13e located at the outermost position, and an optical length of the core 13 increases from an inner circuit to an outer circuit.

One of the inner end 13d and the outer end 13e of the core 13 is an input end of the optical waveguide and the other is an output end of the optical waveguide. In the present embodiment, the inner end 13d is the input end, and the outer end 13e is the output end. The optical waveguide sensor 10 further includes a coupler 15 that guides light from a light source to the input end of the optical waveguide. The coupler 15 reflects light from a light source disposed, for example, right above the substrate 11 and guides the reflected light to the core 13. In FIG. 1, the light source and a light detector for detecting light output from the output end of the optical waveguide are not shown.

The lateral clad 14 is in contact with the whole area of the side surfaces 13a of the core 13 along an extending direction of the core 13 so that light does not leak from the side surfaces 13a. In the present embodiment, the lateral clad 14 and the core 13 have the same thickness. A surface of the lateral clad 14 on an opposite side from the lower clad layer 12 is on the same plane as the upper surface 13b of the core 13. The lateral clad 14 is made of, for example, siliconoxynitride (SiON).

In the optical waveguide sensor 10, the core 13, the lateral clad 14 being contact with the side surfaces 13a of the core 13, and the lower clad layer 12 being contact with the lower surface 13c of the core 13 configurate the optical waveguide. The upper surface 13b of the core 13 is exposed to the outside, and the exposed upper surface 13b function as the transmission surface from which the evanescent wave leaks.

Thus, when light is output from the light source and is guided to the optical waveguide, the evanescent wave as a part of the light leaks from the upper surface 13b of the core 13 and is absorbed by gas or liquid as a detected object being in contact with the upper surface 13b. An intensity of light guided through the optical waveguide is reduced in accordance with the amount of light absorbed by the detected object. Thus, the detected object can be analyzed by measuring the intensity of the light guided through the optical waveguide for a predetermined wavelength band region depending on an absorption property of the detected object.

Figure 3A:
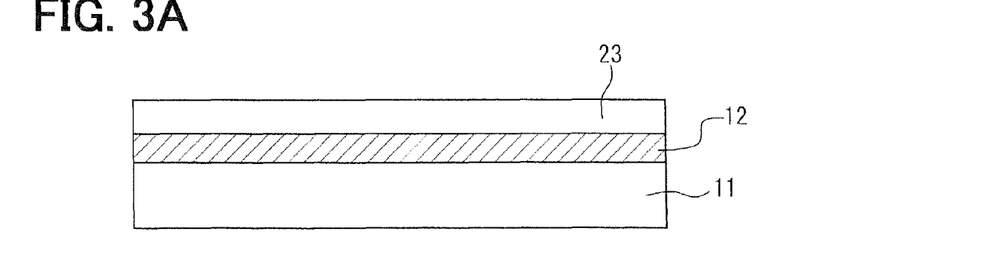

A manufacturing method of the optical waveguide sensor 10 will be described with reference to FIG. 3A to FIG. 3C. During a process shown in FIG. 3A, the substrate 11 made of single crystal silicon is prepared. On the surface of the substrate 11, the lower clad layer 12 made of silicon oxide is formed, for example, by thermal oxidation or chemical vapor deposition (CVD). Next, a silicon nitride layer 23 is formed on the lower clad layer 12, for example, by CVD.

Figure 3B:
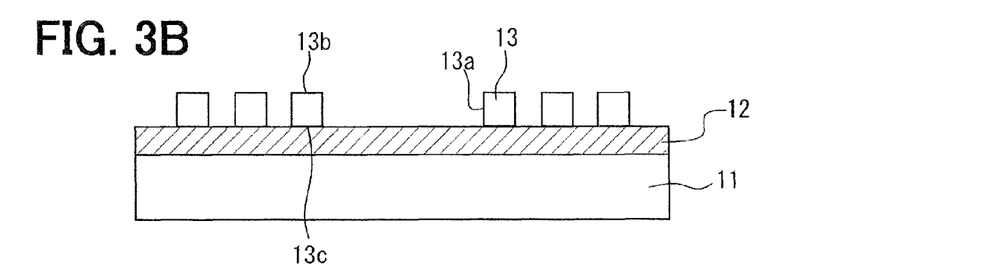

During a process shown in FIG. 3B, the core 13 having the spiral shape is formed by etching the silicon nitride layer 23. In the present state, the lower surface 13c of the core 13 is in contact with the lower clad layer 12, and the side surfaces 13a and the upper surface 13b of the core 13 are exposed to the outside.

Figure 3C:
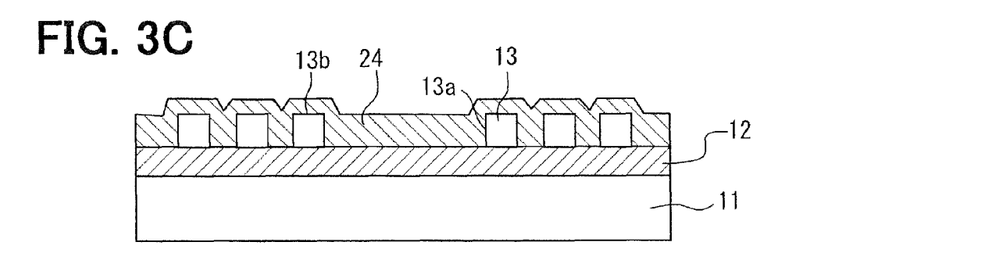

During a process shown in FIG. 3C, a siliconoxynitride layer 24 is formed on the upper clad layer 12, for example, by CVD so as to cover the core 13. In the present embodiment, when the siliconoxynitride layer 24 is formed, a volume ratio of oxygen in all gas in a chamber is constant.

The siliconoxynitride layer 24 is etched so that the upper surface 13b of the core 13 is exposed to the outside, and thereby the optical waveguide sensor 10 can be manufactured.

In the present embodiment, the upper surface 13b of the core 13 is used as the transmission surface and the side surfaces 13a are not used as a transmission surface.

The side surfaces 13a of the core 13 are processed surfaces at a time when the core 13 is formed by patterning. Thus, the side surfaces 13a are rough compared with the upper surface 13b. Thus, if the side surfaces 13a are used as transmission surfaces, scattering may occur at an interface of the side surfaces 13a and a detected object being in contact with the side surfaces 13a, and a transmission loss may increase.

In the optical waveguide sensor 10 according to the present embodiment, the upper surface 13b of the core 13 is used as the transmission surface. Thus, the optical waveguide sensor 10 can restrict the scattering and the transmission loss compared with the configuration that uses the side surfaces 13a of the core 13 as the transmission surface. Accordingly, the ratio of the evanescent wave to the whole amount of light can be increased and the detection accuracy can be improved.

Furthermore, the core 13 extends in the spiral shape. Thus, even when the bending radius is increased so that the core 13 does not transmit light easily, the dimension of the core 13 can be reduced compared with a case where the core 13 extends in a meandering shape. In other words, because a waveguide length can be increased with the same dimension, the detection accuracy can be improved.

As an example, a waveguide length of the core 13 fit in a square on 5 mm on a side is compared between a case where the core 13 extends in a meandering shape and a case where the core 13 extends in a spiral shape. A being radius of each bent portion is set to 400 μm, and a width of the optical waveguide, that is, a distance from center to center of the lateral clad 14 located on opposite sides of the core 13 (the pitch P1 in FIG. 2) is set to 100 μm. As a result, the waveguide length is 36 mm in the case where the core 13 extends in a meandering shape, and the waveguide length is 242 mm in the case where the core 13 extends in a spiral shape.

Furthermore, because the bending radius can be increased, the difference in refractive index between the core 13 and the lateral clad 14 can be reduced. Similarly, the difference in refractive index between the core 13 and the lower clad layer 12 can be reduced. Thus, the transmission loss due to scattering at the interfaces can be restricted and the detection sensitivity can be improved.

As described above, the optical waveguide sensor 10 according to the present embodiment can reduce the dimension while improving the detection sensitivity.

Furthermore, because the upper surface 13b of the core 13 is exposed to the outside of the lateral clad 14, the evanescent wave that leaks from the upper surface 13b as the transmission surface can be efficiently absorbed by a detected object. Thus, the detection sensitivity can be improved.

Second Embodiment

An optical waveguide sensor 10 according to a second embodiment of the present invention will be described with reference to FIG. 4. In the optical waveguide sensor 10 according to the present embodiment, the upper surface 13b and the lower surface 13c of the core 13 function as transmission surfaces. Furthermore, the optical waveguide sensor 10 includes a support layer 16 that restricts buckling of a membrane MEM.

Figure 4:
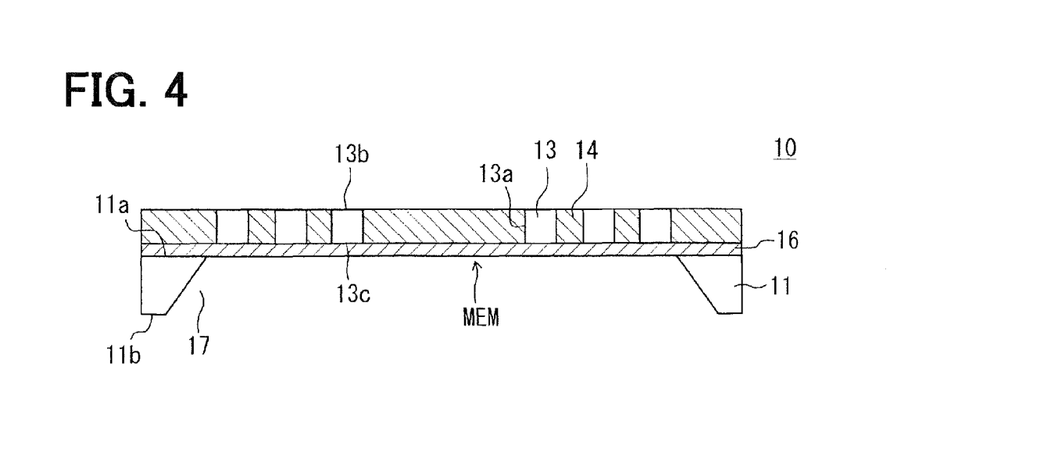
FIG. 4 is a cross-sectional view showing an optical waveguide sensor according to a second embodiment.

The optical waveguide sensor 10 shown in FIG. 4 includes a substrate 11 having an upper surface 11a above which a core 13 and a lateral clad 14 are disposed. The substrate 11 has a removed section 17 that opens on the upper surface 11a. Thus, portions of the core 13 and the lateral clad 14 bridging the removed section 17 form the membrane MEM. Not only the upper surface 13b but also the lower surface 13c of the core 13c in the membrane MEM can function as the transmission surfaces.

In the example shown in FIG. 4, the removed section 17 also opens on a lower surface 11b, which is an opposite side of the substrate 11 from the upper surface 11a. Thus, the removed section 17 provides a through hole penetrating the substrate 11. A most part of the core 13 except for a predetermined region from the outer end 13e is located in a region of the membrane MEM.

The removed section 17 can be provided after the core 13 and the lateral clad 14 are formed, by etching the substrate 11 from the lower surface 11b using the support layer 16 as a stopper.

The support layer 16 is provided instead of the lower clad layer 12. The support layer 16 is disposed between the upper surface 11a of the substrate 11 and the core 13 and the lateral clad 14 so as to cover the whole area of lower surfaces of the core 13 and the lateral clad 14. The support layer 16 can function as a reinforcement layer that restricts bucking of the core 13 and the lateral clad 14 by membrane stress due to materials of the core 13 and the lateral clad 14. The support layer 16 has a thickness not to influence transmission of the evanescent wave that leaks from the lower surface 13c of the core 13. The support layer 16 is made of, for example, silicon nitride.

In the optical waveguide sensor 10 shown in FIG. 4, the evanescent wave that leaks from the upper surface 13b of the core 13 is absorbed by a detected object being in contact with the upper surface 13b and the evanescent wave that leaks from the lower surface 13c of the core 13 is absorbed by the detected object through the support layer 16. In a case where the upper surface 13b and the lower surface 13c of the core 13 are used as the transmission surfaces as described above, the ratio of the evanescent wave that leaks from the transmission surfaces to the whole amount of light can be about two times as large as a case where only the upper surface 13b is used as the transmission surface. Thus, the detection sensitivity can be improved.

The removed section 17 of the substrate 11 is a through hole. Thus, the detected object can be easily arranged on the lower surface 13c of the core 13.

Furthermore, the thickness of the support layer 16 has a thickness not to influence the transmission of the evanescent wave that leaks from the lower surface 13c. Thus, the optical waveguide sensor 10 can improve the detection sensitivity while restricting buckling of the membrane MEM including the core 13 and the lateral clad 14.

The thickness not to influence the transmission of the evanescent wave can also be rephrased as a thickness with which a reflection does not occur on an interface between the core 13 and the support layer 16. When the wavelength of the light guided in the optical waveguide is $\lambda$, the refractive index of the support layer 16 with the wavelength $\lambda$ is $n_s$, and the thickness of the support layer is $t_s$, the thickness $t_s$ is determined so that a relationship of $n_s \times t_s \leq \lambda$, is satisfied.

When the support layer 16 is formed so that $n_s \times t_s$, that is, the optical wavelength is equal to or less than the wavelength $\lambda$, the evanescent wave can permeate through the support layer 16 efficiently even when the support layer 16 is provided, and the evanescent wave can be absorbed by the detected object.

Figure 5:
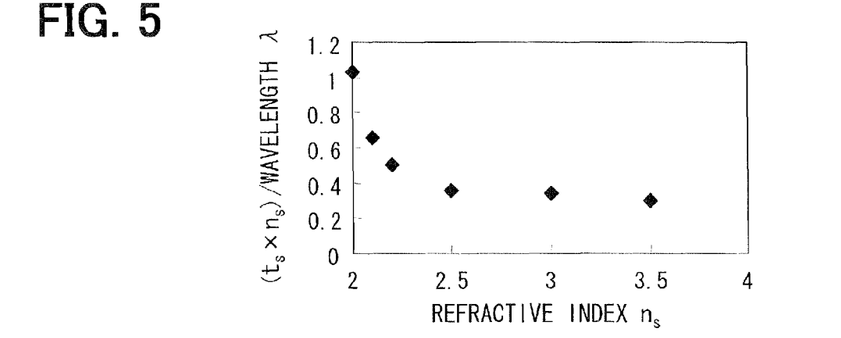
FIG. 5 is a graph showing a relationship between a refractive index $n_s$ of a support layer and a ratio of an optical length of a support layer to a wavelength $\lambda$.

The thickness $t_s$ of the support layer 16 may also be determined so as to satisfy a relationship of $n_s \times t_s \leq 0.3\lambda$. According to a simulation by the inventors, the value of the optical length $(n_s \times t_s)$/wavelength $\lambda$ with respect to the refractive index $n_s$ of the support layer 16 converges at 0.3, as shown in FIG. 5. Thus, when the thickness $t_s$ is determined so as to satisfy the above-described relationship, the detection sensitivity can be improved regardless of the wavelength $\lambda$ and the refractive index $n_s$ of the support layer 16.

Figure 6:
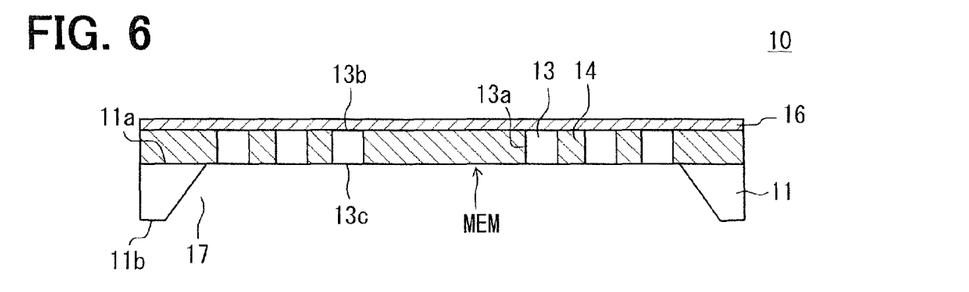
FIG. 6 is a cross-sectional view showing an optical waveguide sensor according to a first modification of the second embodiment.

In the example shown in FIG. 4, the support layer 16 is disposed on the lower surface side of the core 13, that is, between the substrate 11 and the core 13 and the lateral clad 14. As a first modification shown in FIG. 6, the support layer 16 may also be disposed on an upper surface side of the core 13 so as to cover the whole area of the core 13 and the lateral clad 14. In the present case, the evanescent wave that leaks from the upper surface 13b of the core 13 is absorbed by the detected object through the support layer 16, and the evanescent wave that leaks from the lower surface 13c of the core 13 is absorbed by the detected object being in contact with the lower surface 13c.

Figure 7:
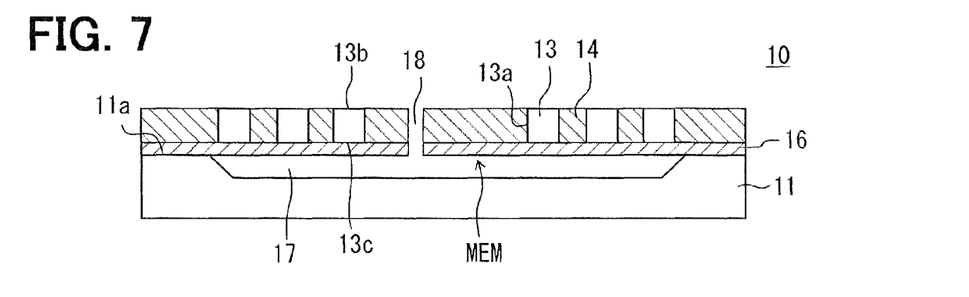
FIG. 7 is a cross-sectional view showing an optical waveguide sensor according to a second modification of the second embodiment.

The removed section 17 of the substrate 11 is not limited to the through hole shown in FIG. 4. For example, as a second modification shown in FIG. 7, the substrate 11 may have a recess portion that opens only on the upper surface 11a, and the recess portion may provide the removed section 17. The removed section 17 may be formed after the core 13 and the lateral clad 14 are formed, for example, by etching the substrate 11 from the upper surface 11a through an etching hole 18. The etching hole 18 penetrates a portion of the lateral clad 14 that does not influence the optical waveguide. The etching hole 18 also penetrates the support layer 16. The etching hole 18 is provided at a plurality of portions. In the present configuration, the support layer 16 may be disposed on the upper surface side of the core 13.

Figure 8:
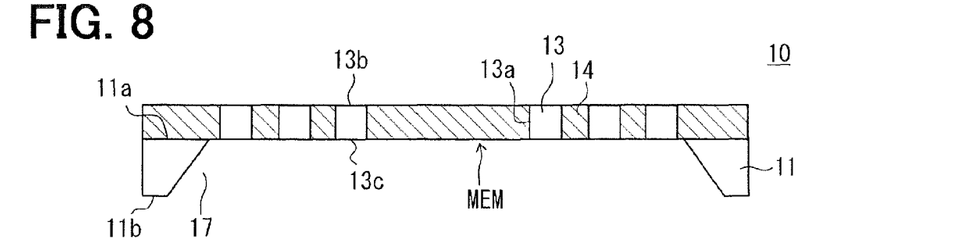
FIG. 8 is a cross-sectional view showing an optical waveguide sensor according to a third modification of the second embodiment.

In a case where there is no possibility of buckling, as a third modification shown in FIG. 8, the membrane MEM may include the core 13 and the lateral clad 14, and the support layer 16 may be omitted. In the present configuration, both the upper surface 13b and the lower surface 13c of the core 13 are exposed. Thus, the amount of evanescent wave absorbed by the detected object can be increased compared with a configuration including the support layer 16.

Third Embodiment

The inventors studied about more preferred configuration in the configurations described in the first embodiment and the second embodiment with simulation. An optical waveguide according to a third embodiment of the present invention is based on the simulation result. In the following simulation, an optical waveguide sensor 10 in which both an upper surface 13b and a lower surface 13c of a core 13 are exposed surfaces as shown in FIG. 8 is used as a model.

A relationship between a refractive index of the core 13 and a refractive index of a lateral clad 14 according to the present embodiment will be described below. The refractive index of the core 13 is indicated by $n_1$, the refractive index of the lateral clad 14 is indicated by $n_2$ ($<n_1$), and a difference in refractive index between the core 13 and the lateral clad 13 is indicated by $\Delta n$ ($=n_1-n_2$).

Figure 9:
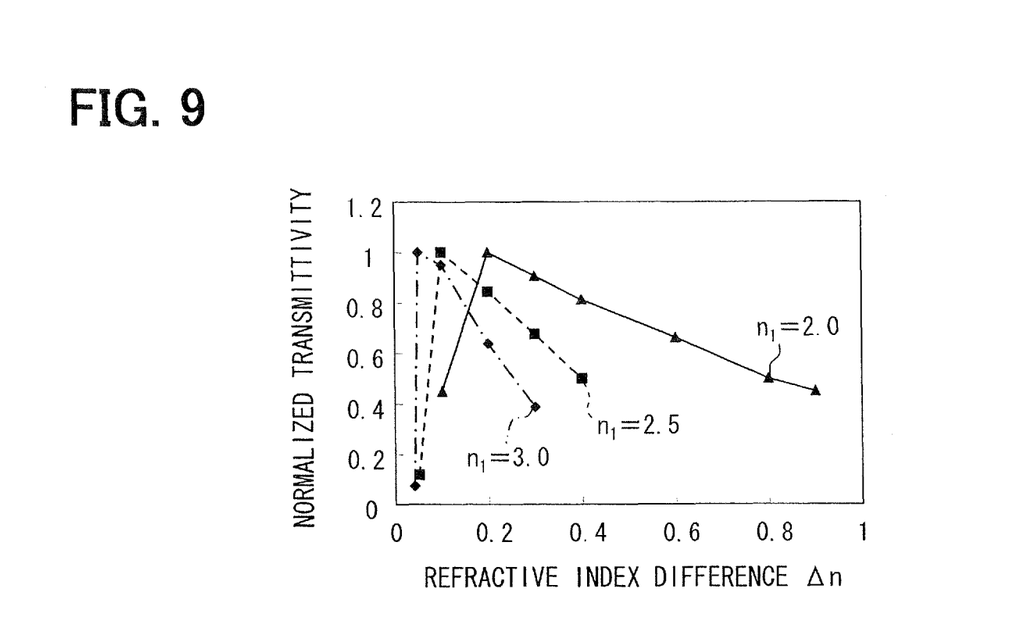
FIG. 9 is a graph showing a relationship between a difference Δn in refractive index between a core and a lateral clad and a normalized transmittivity in an optical waveguide sensor according to a third embodiment.

In FIG. 9, a relationship between the refractive index difference and a normalized transmittivity is shown in a case where a wavelength $\lambda$ of light guided in the optical waveguide is 4.5 μm, and the refractive index $n_1$ of the core 13 is changed among three levels, that is, 2.0, 2.5, and 3.0. The normalized transmittivity is a transmittivity normalized by setting the maximum transmittivity for each refractive index of the core 13 to 1. In a case where the refractive index $n_1$ of the core 13 is 2.0, the maximum transmittivity (the normalized transmittivity=1) is provided when the refractive index difference $\Delta n$ is 0.2. In a case where the refractive index $n_1$ of the core 13 is 2.5, the maximum transmittivity (the normalized transmittivity=1) is provided when the refractive index difference $\Delta n$ is 0.1. In a case where the refractive index $n_1$ of the core 13 is 3.0, the maximum transmittivity (the normalized transmittivity=1) is provided when the refractive index difference $\Delta n$ is 0.05.

Figure 10:
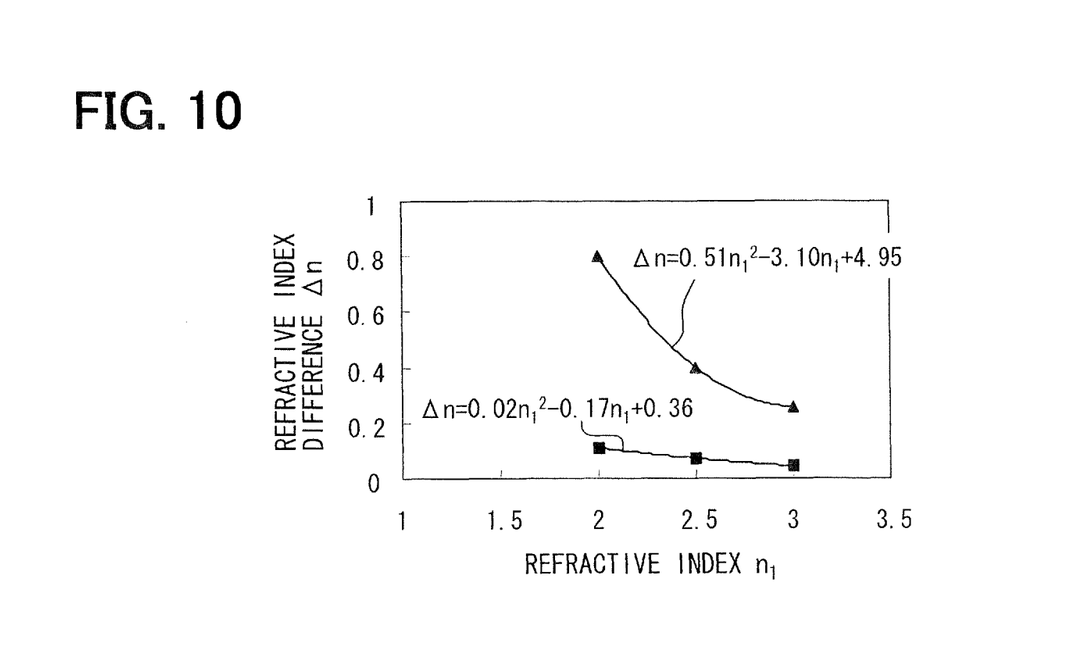
FIG. 10 is a graph showing a relationship between a refractive index $n_1$ of the core and the difference Δn in refractive index between the core and the lateral clad in a case where the normalized transmittivity is 0.5.

The refractive indices at which the normalized transmittivity is 0.5 (½ of the maximum transmittivity) are extracted from the graph shown in FIG. 9 and are fitted as a quadratic function by a least-square method in FIG. 10. In FIG. 9, data of each refractive index of the core 13 has two intersections with the normalized transmittivity=0.5, one of the two intersections is at a small refractive index difference $\Delta n$ and the other is at a large refractive index difference $\Delta n$.

In a case where the intersection at the small refractive index $\Delta n$ of each refractive index (2.0, 2.5, 3.0) is fitted as a quadratic function by a least-square method, as shown in FIG. 10, $\Delta n = 0.02 n_1^2 - 0.17 n_1 + 0.36$. The intersection of the refractive index $n_1=2.0$ is 0.044, the intersection of the refractive index $n_1=2.5$ is 0.072, and the intersection of the refractive index $n_1=3.0$ is 0.11.

In a case where the intersection at the large refractive index difference $\Delta n$ of each refractive index (2.0, 2.5, 3.0) is fitted as a quadratic function by a least-square method, as shown in FIG. 10, $\Delta n = 0.51 n_1^2 - 3.10 n_1 + 4.95$. The intersection of the refractive index $n_1=2.0$ is 0.255, the intersection of the refractive index $n_1=2.5$ is 0.4, and the intersection of the refractive index $n_1=3.0$ is 0.8.

In each refractive index (2.0, 2.5, 3.0) of the core 13, a range between the intersection at the small refractive index difference $\Delta n$ and the intersection at the large refractive index difference $\Delta n$ is a range where the normalized transmittivity is equal to or greater than 0.5. Thus, by forming the core 13 and the lateral clad 14 so as to satisfy equation (1), the normalized transmittivity can be equal to or greater than 0.5, that is, the transmittivity can be equal to or greater than ½ of the maximum transmittivity.

$$0.02 n_1^2 - 0.17 n_1 + 0.36 \leq \Delta n \leq 0.51 n_1^2 - 3.10 n_1 + 4.95 \qquad (1).$$

In the present embodiment, the core 13 and the lateral clad 14 are formed so as to satisfy the equation (1). Thus, the transmittivity of light guided in the optical waveguide is high, a transmission loss can be reduced, and a detection sensitivity can be improved.

Next, a thickness of the core 13 according to the present embodiment will be described.

Figure 11:
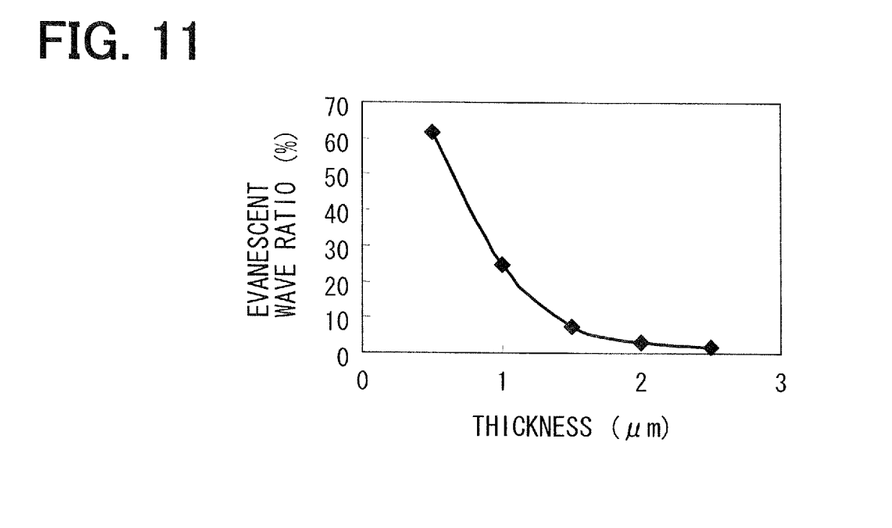
FIG. 11 is a graph showing a relationship between a thickness of the core and a ratio of an evanescent wave to the whole amount of light.

FIG. 11 is a graph showing a relationship between the thickness of the core 13 and a ratio of the evanescent wave that leaks from the transmission surface to the whole amount of light, that is, the evanescent wave ratio. In FIG. 11, an example in which the refractive index $n_1$ of the core 13 is 3.0, the refractive index $n_2$ of the lateral clad 14 is 2.8, and the wavelength λ of light guided in the optical waveguide is 4.5 µm is shown.

As shown in FIG. 11, a change of the evanescent wave ratio with respect to the thickness of the core 13 drastically changes around the thickness of 2 µm. Specifically, in a case where the thickness of the core 13 is equal to or less than 2 µm, the change of the evanescent wave ratio with respect to the thickness of the core 13 is larger than a case where the thickness of the core 13 is greater than 2 µm. The change of the evanescent wave ratio with respect to the thickness of the core 13 is further increased in a case where the thickness of the core 13 is equal to or less than 1.5 µm.

In the present embodiment, based on the above-described simulation result, the thickness of the core 13 is equal to or less than 2.0 µm. Thus, the evanescent wave ratio can be increased, and the detection sensitivity can be improved. When the thickness of the core 13 is equal to or less than 1.5 µm, the detection sensitivity can be further improved.

Next, the refractive index $n_1$ of the core 13 according to the present embodiment will be described.

Figure 12:
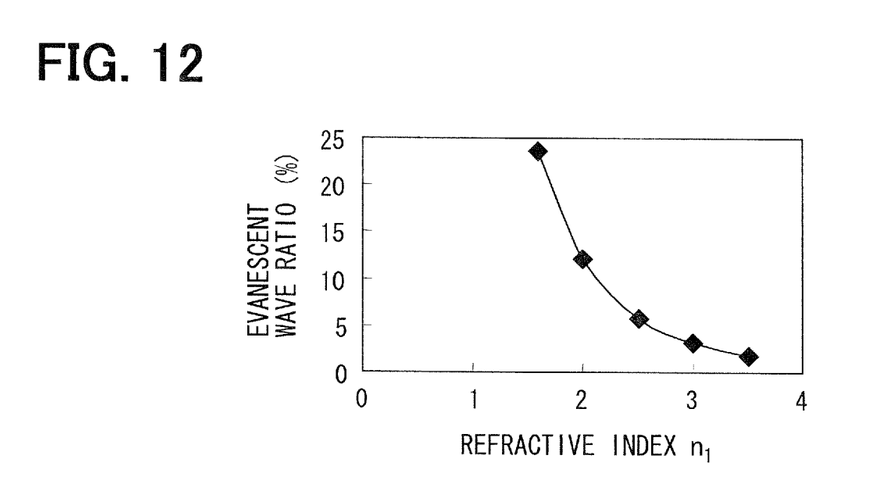
FIG. 12 is a graph showing a relationship between the refractive index $n_1$ of the core and the ratio of the evanescent wave to the whole amount of light.

FIG. 12 is a graph showing a relationship between the refractive index $n_1$ of the core 13 and the evanescent wave ratio. In FIG. 12, an example in which the refractive index difference Δn is 0.2, and the wavelength λ of the light guided in the optical waveguide is 4.5 µm is shown.

As shown in FIG. 12, a change of the evanescent wave ratio with respect to the refractive index $n_1$ of the core 13 drastically changes around the refractive index $n_1$ of 3. Specifically, in a case where the refractive index $n_1$ of the core 13 is equal to or less than 3, the change of the evanescent wave ratio with respect to the refractive index $n_1$ of the core 13 is larger than a case where the thickness of the core 13 is greater than 3.

In the present embodiment, based on the simulation result, the refractive index $n_1$ of the core 13 is equal to or less than 3. Thus, the evanescent wave ratio can be increased and the detection sensitivity can be improved.

Figure 13A:
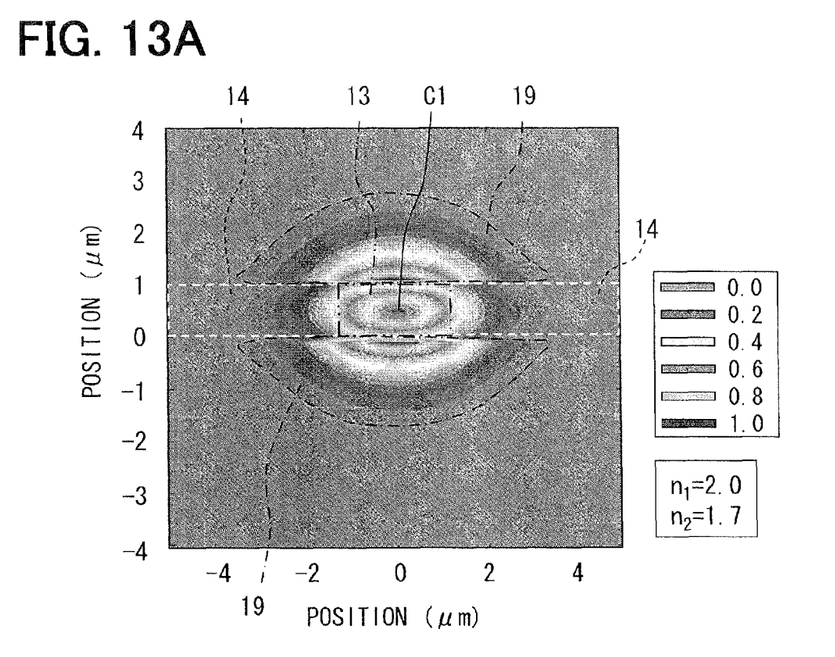
FIG. 13A is a diagram showing a light intensity distribution of the optical waveguide sensor according to the third embodiment.
Figure 13B:
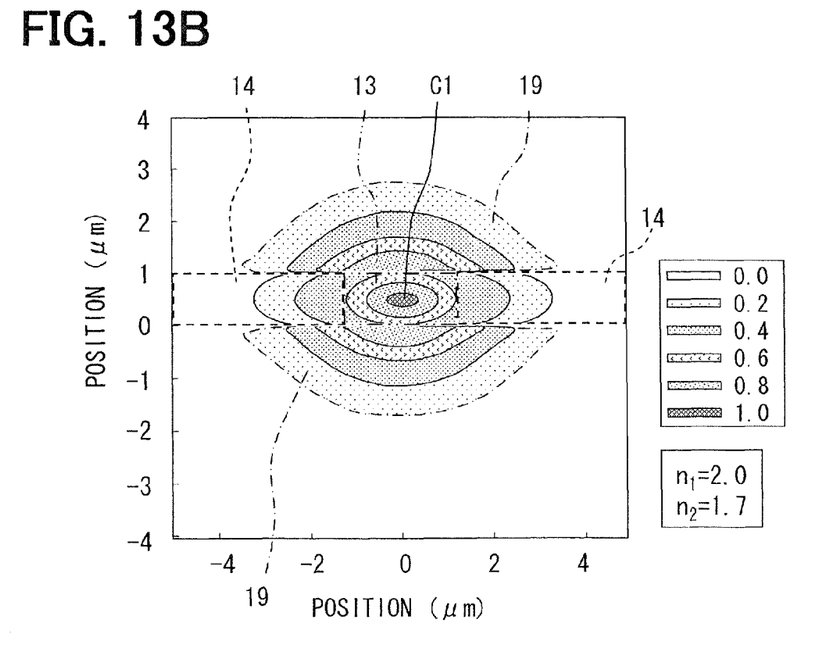
FIG. 13B is an illustrative view of the diagram shown in FIG. 13A.

FIG. 13A is a diagram showing a light intensity distribution of the optical waveguide sensor according to the present embodiment, and FIG. 13B is an illustrative view of the diagram shown in FIG. 13A. Specifically, the refractive index $n_1$ of the core 13 is 2.0, the refractive index $n_2$ of the lateral clad 14 is 1.7, the refractive index difference Δn is 0.3, the thickness of the core 13 is 1.0 µm, the width of the core 13 is 2.5 µm, and the wavelength λ of the light guided in the optical waveguide is 3.5 µm.

Figure 14A:
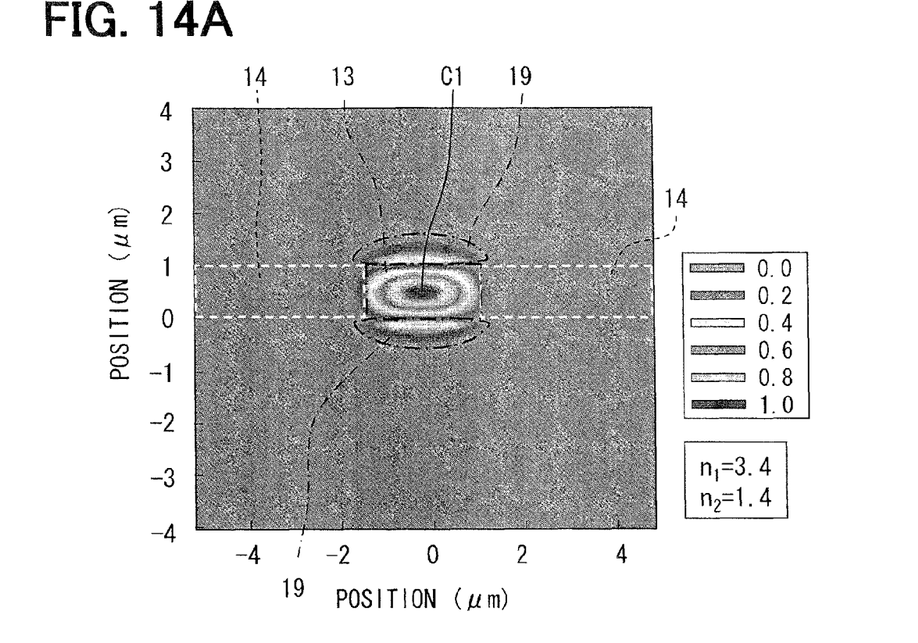
FIG. 14A is a diagram showing a light intensity distribution of an optical waveguide sensor according to a first comparative example.
Figure 14B:
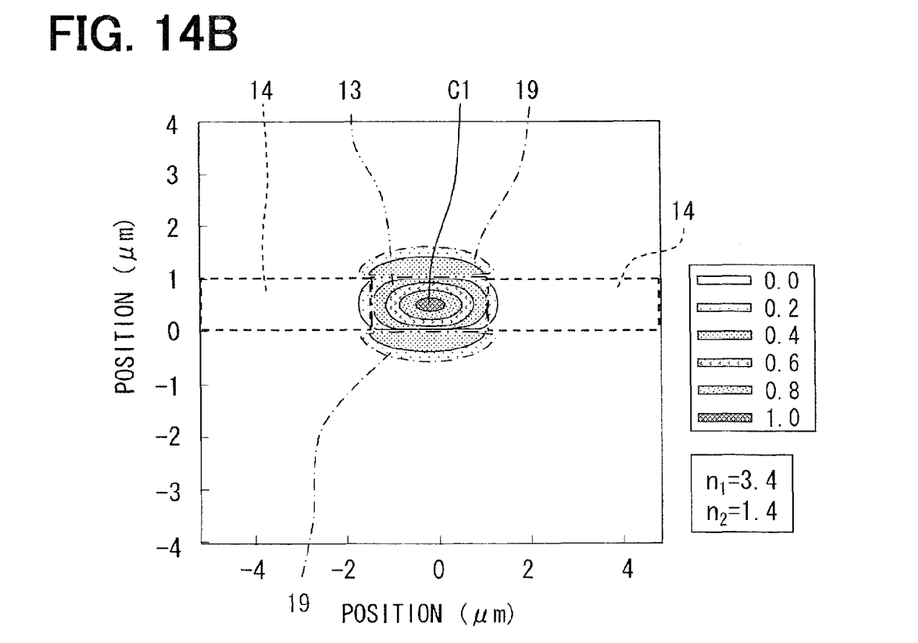
FIG. 14B is an illustrative view of the diagram shown in FIG. 14A.

FIG. 14A is a diagram showing a light intensity distribution of an optical waveguide sensor according to a first comparative example, and FIG. 14B is an illustrative view of the diagram shown in FIG. 14A. In the optical waveguide sensor according to the first comparative example, the lateral clad 14 is disposed on either side surfaces 13a of the core 13, and the upper surface 13b and lower surface 13c are used as transmission surfaces in a manner similar to the configuration shown in FIG. 13A and FIG. 13B. The refractive index $n_1$ of the core 13 is 3.4, the refractive index $n_2$ of the lateral clad 14 is 1.4, the refractive index difference Δn is 2.0, the thickness of the core 13 is 1.0 µm, the width of the core 13 is 2.5 µm, and the wavelength λ of the light guided in the optical waveguide is 3.5 µm.

Figure 15A:
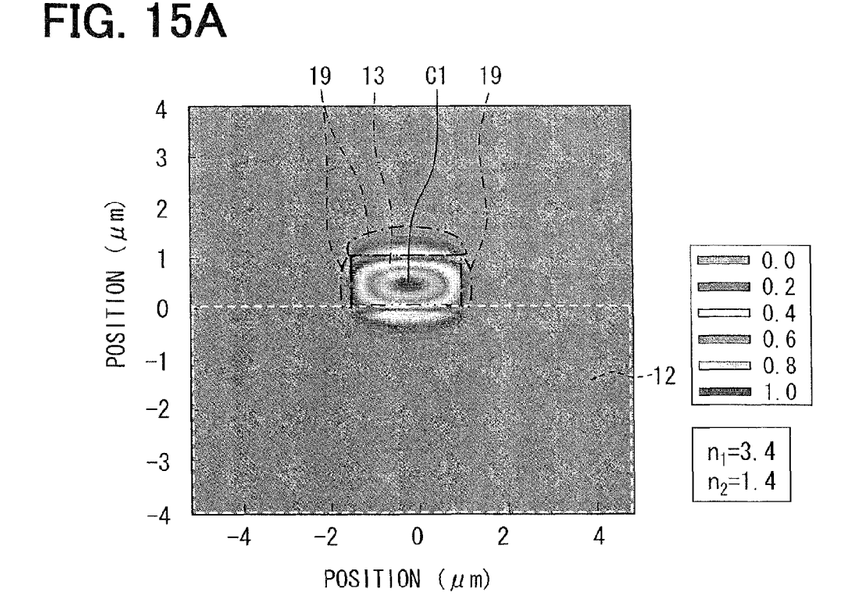
FIG. 15A is a diagram showing a light intensity distribution of an optical waveguide sensor according to a second comparative example.
Figure 15B:
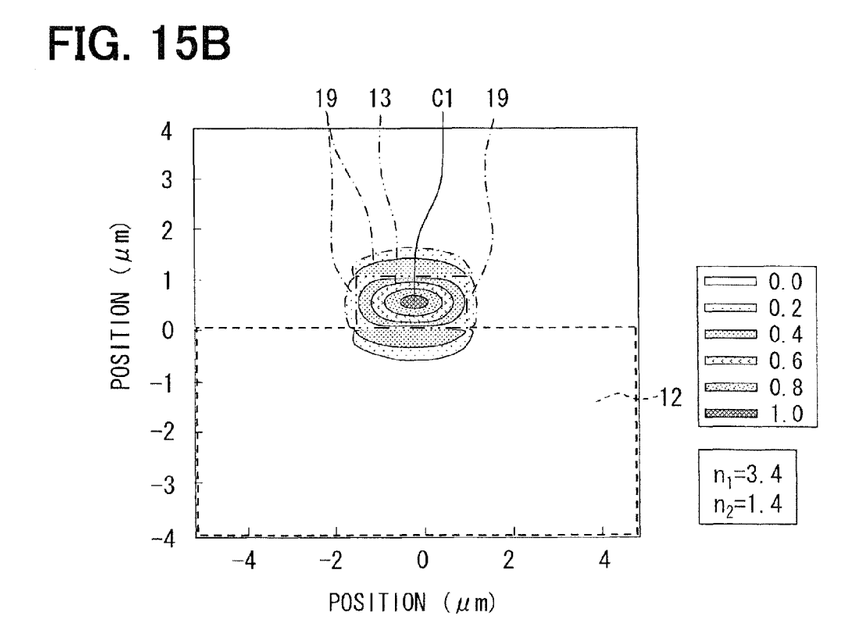
FIG. 15B is an illustrative view of the diagram shown in FIG. 15A.

FIG. 15A is a diagram showing a light intensity distribution of an optical waveguide sensor according to a second comparative example, and FIG. 15B is an illustrative view of the diagram shown in FIG. 15A. In the optical waveguide sensor according to the second comparative example, the core 13 is disposed on the lower clad layer 12, and the both side surfaces 13a and the upper surface 13b of the core 13 are used as transmission surfaces. The refractive index $n_1$ of the core 13 is 3.4, the refractive index $n_2$ of the lateral clad 14 is 1.4, the refractive index difference Δn is 2.0, the thickness of the core 13 is 1.0 µm the width of the core 13 is 2.5 µm and the wavelength λ of the light guided in the optical waveguide is 3.5 µm.

The first comparative example and the second comparative example correspond to conventional configurations having a large refractive index difference Δn. C1 in FIG. 13A to FIG. 15B indicates a center position of the core 13, and FIG. 13A to FIG. 15B show relative intensity distribution in which a light intensity at the center position C1 is set to 1.0. A dashed-dotted line 19 in FIG. 13A to FIG. 15B indicates area of the evanescent wave that leaks from the transmission surfaces of the core 13. In FIG. 13A to FIG. 15B, the light intensity decreases with a distance from the center position C1. The light intensity at a position outside the area of the evanescent wave surrounded by the dashed-dotted line 19 is zero.

Figure 16:
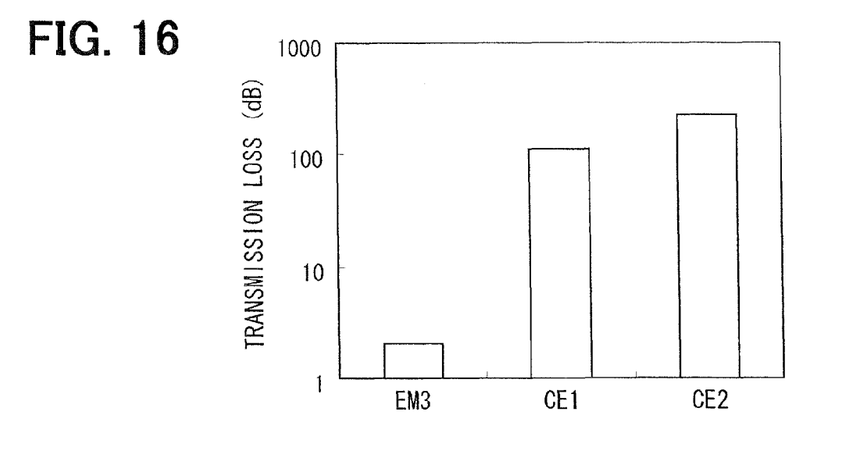
FIG. 16 is a graph showing transmission losses of the optical waveguide sensor according to the third embodiment (EM3), the optical waveguide sensor according to the first comparative example (CE1), and the optical waveguide sensor according to the second comparative example (CE2)
Figure 17:
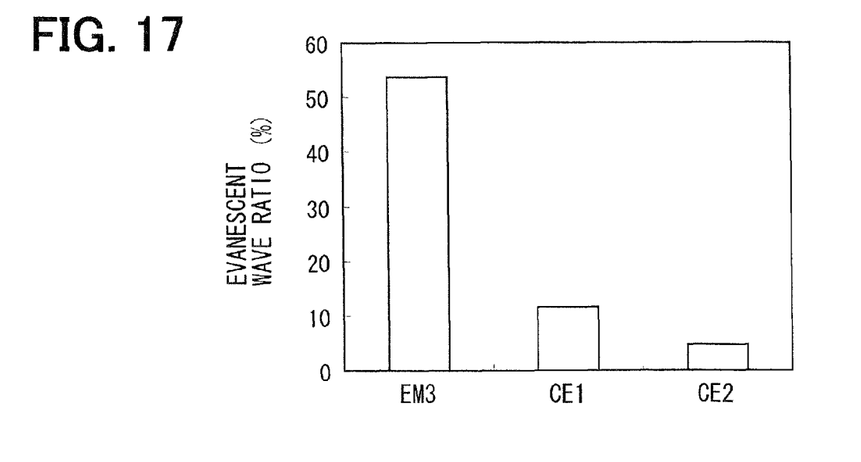
FIG. 17 is a graph showing ratios of a evanescent wave to the whole amount of light in the optical waveguide sensor according to the third embodiment (EM3), the optical waveguide sensor according to the first comparative example (CE1), and the optical waveguide sensor according to the second comparative example (CE2)

FIG. 16 is a graph showing transmission losses of the optical waveguide sensor according to the present embodiment (EM3), the optical waveguide sensor according to the first comparative example (CE1), and the optical waveguide sensor according to the second comparative example (CE2). FIG. 7 is a graph showing ratios of the evanescent wave that leaks from the transmission surfaces to the whole amount of light, that is, the evanescent wave ratios of the optical waveguide sensor according to the present embodiment (EM3), the optical waveguide sensor according to the first comparative example (CE1), and the optical waveguide sensor according to the second comparative example (CE2).

As is clear from a comparison of FIG. 13A to FIG. 15B and the result shown in FIG. 16 and FIG. 17, the optical waveguide sensor 10 according to the present embodiment can increase the ratio of the evanescent wave to the whole amount of light. Thus, the optical waveguide sensor 10 according to the present embodiment can improve the detection sensitivity compared with the first comparative example and the second comparative example.

In the present embodiment, the optical waveguide sensor 10 in which both the upper surface 13b and the lower surface 13c of the core 13 are exposed outside and function as the transmission surfaces is used as the model, as an example. Even in a case where only one of the upper surface 13b and the lower surface 13c functions a transmission surface, the detection sensitivity can be improved compared with the first comparative example and the second comparative example. In the case where the only one of the upper surface 13b and the lower surface 13c functions as the transmission surface, the ratio of the evanescent wave that leaks from the transmission surface to the whole amount of light becomes about half of the configuration shown in FIG. 13A and FIG. 13B, that is, from 20% to 30%.

Fourth Embodiment

Figure 18:
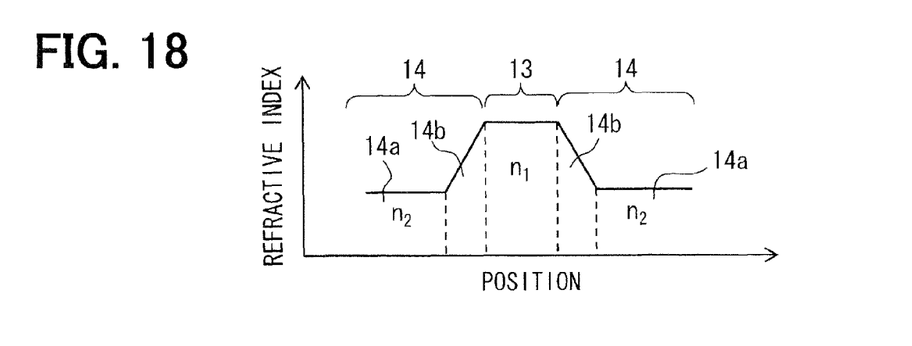
FIG. 18 is a diagram showing a refractive index at each component in an optical waveguide sensor according to a fourth embodiment.

In the above-described embodiments, the refractive index of the lateral clad 14 being in contact with the side surfaces 13a of the core 13 is constant. In an optical waveguide according to a fourth embodiment of the present invention, as shown in FIG. 18, the lateral clad 14 includes a refractive-index constant portion 14a and a refractive-index inclination portion 14b.

The refractive-index constant portion 14a has a predetermined refractive index $n_2$ ($<n_1$). The refractive-index inclination portion 14b is disposed between the refractive-index constant portion 14a and the core 13. The refractive-index of the refractive index inclination portion 14b decreases continuously or in a stepwise manner from the refractive index $n_1$ to the refractive index $n_2$ with a distance from the side surface 13a of the core 13.

The transmission loss due to scattering at the interfaces of the core 13 and the lateral clad 14 increases with increasing the refractive index difference Δn of the core 13 and the lateral clad 14 being in contact with the side surface 13a of the core 13. In the present embodiment, the refractive index of the lateral clad 14 decreases continuously or in a stepwise manner from the interfaces with the core 13. Thus, the scattering can be restricted and the detection sensitivity can be improved.

Figure 19A:
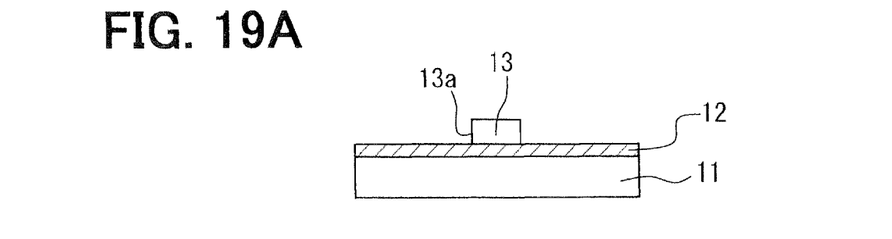
Figure 19B:
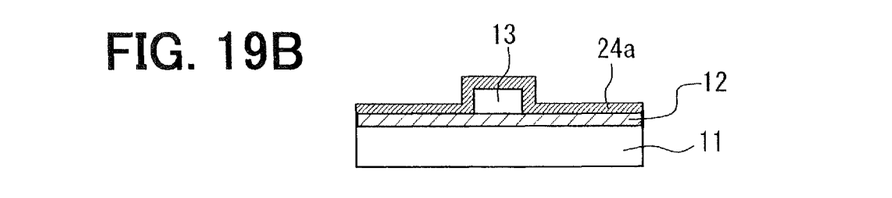

The optical waveguide sensor 10 according to the present embodiment can be manufactured, for example, by a method shown in FIG. 19A to FIG. 19B. In FIG. 19A to FIG. 19B, only one core 13 is shown for the sake of convenience.

During a process shown in FIG. 19A, the lower clad layer 12 and the core 13 are formed on the substrate 11 in a manner similar to the first embodiment. After forming the core 13, a siliconoxynitride layer is deposited by CVD above the lower clad layer 12 so as to cover the core 13. In the present case, a volume ratio of oxygen in all gas in a chamber is increased while the siliconoxynitride layer is formed.

Figure 19C:
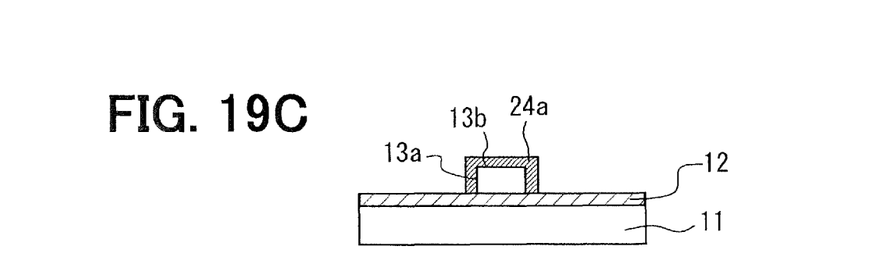

For example, during a process shown in FIG. 19B, in a state where gas for supplying oxygen accounts for 20% of all gas in the chamber, a siliconoxynitride layer 24a is deposited on the lower clad layer 12 so as to cover the core 13. Then, as shown in FIG. 19C, a portion of the siliconoxynitride layer 24a covering the lower clad layer 12 is removed by etching so that a portion of the siliconoxynitride layer 24a covering the core 13 remain.

Next, in a state where gas for supplying oxygen accounts for 50% of all gas in the chamber, a siliconoxynitride layer 24b is deposited on the lower clad layer 12 so as to cover the siliconoxynitride layer 24a. The siliconoxynitride layer 24b is treated with a patterning process so that a part of the siliconoxynitride layer 24b covering the lower clad layer 12 is removed and only a part of the siliconoxynitride layer 24b covering the core 13 remains.

Figure 19D:
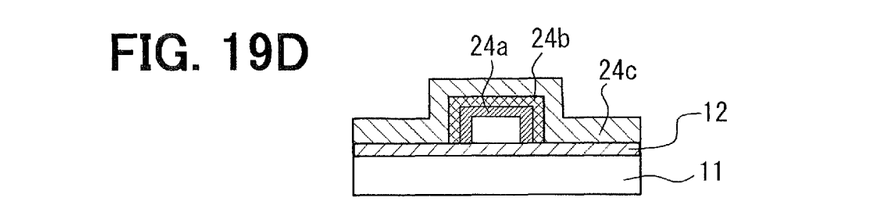
Figure 19E:
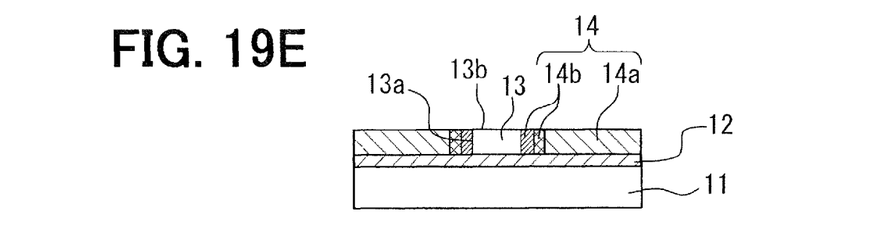

Next, in a state where gas for supplying oxygen accounts for 80% of all gas in the chamber, as shown in FIG. 19D, a siliconoxynitride layer 24c is deposited on the lower clad layer 12 so as to cover the siliconoxynitride layer 24b. The siliconoxynitride layer 24c and the siliconoxynitride layer 24b are etched so that side surfaces 13a of the core 13 is covered with the siliconoxynitride layer 24c and the siliconoxynitride layer 24b and the upper surface 13b of the core 13 is exposed outside. During a process shown in FIG. 19E, an etching is performed so that the upper surface 13b of the core 13 and the lateral clad 14 are located on the same plane.

In this way, by changing the composition of material for forming the lateral clad 14 continuously or in a stepwise manner, the refractive-index constant portion 14a including the siliconoxynitride layer 24c and the refractive-index inclination portion 14b including the siliconoxynitride layer 24a, 24b are formed, and thereby the optical waveguide sensor 10 according to the present embodiment is formed.

In the above-described example, only the upper surface 13b functions as the transmission surface. The refractive-index inclination portion 14b can also be applied to a configuration in which the upper surface 13b and the lower surface 13c of the core 13 function as the transmission surfaces.

Although the present invention has been fully described in connection with the preferred embodiments thereof with reference to the accompanying drawings, the present invention is not limited to the above-described embodiments and can be modified within a scope of the present invention.

What is claimed is:

1. An optical waveguide sensor comprising:
a substrate; and
an optical waveguide including a core and a lateral clad, the core extending in a spiral shape above a surface of the substrate, the lateral clad disposed in a same layer as the core above the surface of the substrate and being in contact with either side surfaces of the core, at least a part of a surface of the core located opposite from the substrate being a transmission surface from which light leaks and is absorbed by a detected object, wherein
the substrate has a removed section that opens on the surface of the substrate,
portions of the core and the lateral clad bridging the removed section form a membrane, and
both the surface of the core located opposite from the substrate and a surface of the core facing the substrate are the transmission surfaces, and further comprising:
a support layer disposed on at least one of the transmission surfaces of the core for reinforcing the membrane, wherein
when the light guided in the optical waveguide has a wavelength λ, the support layer has a refractive index $n_s$ at the wavelength λ, and the support layer has a thickness $t_s$, the support layer satisfies a relationship of $n_s \times t_s \leq \lambda$.

2. The optical waveguide sensor according to claim 1, wherein
when the core has a refractive index $n_1$, the lateral clad has a refractive index $n_2$, and a difference between the refractive index $n_1$ and the refractive index $n_2$ is indicated by Δn, the optical waveguide satisfies a relationship of:

$$0.02n_1^2 - 0.17n_1 + 0.36 \leq \Delta n \leq 0.51n_1^2 - 3.10n_1 + 4.95.$$

3. The optical waveguide sensor according to claim 1, wherein
the core has a thickness of equal to or less than 2.0 μm.

4. The optical waveguide sensor according to claim 1, wherein
the refractive index $n_1$ of the core is less than or equal to 3.

5. The optical waveguide sensor according to claim 1, wherein
the lateral clad has a refractive-index inclination portion in a predetermined region from a boundary with the core, and a refractive index of the refractive-index inclination portion decreases continuously or in a stepwise manner with a distance from the core.

6. The optical waveguide sensor according to claim 1, wherein
the removed section is a through hole that penetrates the substrate from the surface to an opposite surface.

7. The optical waveguide sensor according to claim 1, wherein
the support layer satisfies a relationship of $n_s \times t_s \leq 0.3\lambda$.

8. The optical waveguide sensor according to claim 1, further comprising
a light source that inputs the light to an input end of the optical waveguide, and
a light detector that detects the light output from an output end of the optical waveguide.

* * * * *